United States Patent
Yao et al.

(10) Patent No.: US 6,875,896 B2
(45) Date of Patent: Apr. 5, 2005

(54) METHOD FOR PRODUCING HIGH PURITY 1,1-BIS(4-HYDROXYPHENYL) CYCLOHEXANES

(75) Inventors: Kazuhiko Yao, Wakayama (JP); Tooru Nakaguchi, Wakayama (JP); Kenji Ekawa, Wakayama (JP)

(73) Assignee: Honshu Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 10/879,436

(22) Filed: Jun. 29, 2004

(65) Prior Publication Data
US 2005/0004405 A1 Jan. 6, 2005

(30) Foreign Application Priority Data
Jul. 3, 2003 (JP) ........................................ 2003-190786

(51) Int. Cl.$^7$ .............................................. C07C 39/17
(52) U.S. Cl. ....................................................... 568/721
(58) Field of Search ................................ 568/721, 724, 568/723

(56) References Cited

U.S. PATENT DOCUMENTS

| | | | | |
|---|---|---|---|---|
| 3,673,262 A | * | 6/1972 | Prahl et al. | 568/721 |
| 4,113,974 A | * | 9/1978 | Mark et al. | 568/750 |
| 4,535,190 A | * | 8/1985 | Arai et al. | 568/721 |
| 4,982,014 A | * | 1/1991 | Freitag et al. | 568/721 |

* cited by examiner

*Primary Examiner*—Michael L. Shippen
(74) *Attorney, Agent, or Firm*—Knobbe, Martens, Olson & Bear LLP

(57) ABSTRACT

A method for producing a high purity 1,1-bis(4-hydroxyphenyl)cyclohexane represented by the general formula (II),

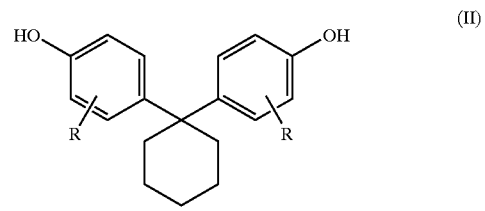

(II)

wherein R is a hydrogen atom or alkyl group, comprising the steps of: reacting cyclohexanone and a phenol represented by the general formula (I) in the presence of an acid catalyst;

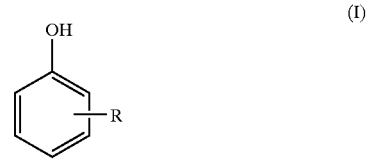

(I)

wherein R is the same as defined above, neutralizing the resultant reaction mixture with an alkali; primarily crystallizing and filtering a 1,1-bis(4-hydroxyphenyl)cyclohexane produced to obtain a primary crystallization filtrate; dissolving 100 parts by weight of the primary crystallization filtrate in a mixed solvent, which comprises 5 to 10 parts by weight of water and 100 to 200 parts by weight of a lower aliphatic ketone solvent, or 200 to 400 parts by weight of a lower aliphatic alcohol solvent; filtering the resulting solution through a zeta potential filter; and secondarily crystallizing and filtering the 1,1-bis(4-hydroxyphenyl)cyclohexane from the resulting filtrate in the presence of water.

8 Claims, No Drawings

METHOD FOR PRODUCING HIGH PURITY 1,1-BIS(4-HYDROXYPHENYL) CYCLOHEXANES

BACKGROUND OF THE INVENTION

1. Field of the Invention

The present invention relates to a method for producing a high purity 1,1-bis(4-hydroxyphenyl)cyclohexane that is useful as a material for various polymers, such as aromatic polycarbonates, aromatic polyether sulfones, aromatic polyether ketones, and aromatic polyether imides, advantageously on an industrial scale with improved production yield and efficiency.

2. Description of the Related Art

A 1,1-bis(4-hydroxyphenyl)cyclohexane is a kind of bisphenol and generally obtained by reacting cyclohexanone and a phenol in the presence of an acid catalyst. In order to obtain a high purity 1,1-bis(4-hydroxyphenyl)cyclohexane on an industrial scale, there has been a conventionally known method in which, for example, cyclohexanone and a phenol are reacted in the presence of an acid catalyst, a reaction product obtained is neutralized with an alkali, the resulting 1,1-bis(4-hydroxyphenyl)cyclohexane is primarily crystallized and filtered, the reaction product is washed with methylene chloride, and then recrystallized from a mixed solvent of methanol and water to obtain a 99.2% pure 1,1-bis(4-hydroxyphenyl)cyclohexane. Further, it is known that the abovementioned reaction product can be washed with methylene chloride and dried to similarly obtain a high purity product (see Japanese Patent Application Laid-open No. 64-22833).

On the other hand, it is also known that a 99.3% pure 1,1-bis(4-hydroxyphenyl)cyclohexane can be obtained by the mixed crystallization of a 1,1-bis(4-hydroxyphenyl)cyclohexane and a phenol followed by the heating in vacuum (see Japanese Patent Application Laid-open No. 5-78270).

In recent years, with the expansion of the use of 1,1-bis(4-hydroxyphenyl)cyclohexanes, there has been a strong demand for producing products having further higher purity on an industrial scale with further improved production yield and efficiency. However, the abovementioned methods cannot meet such a demand, and furthermore, there has been so far no measure reported regarding the removal of a very small amount of metal impurities in a reaction product, which is derived from an alkali such as sodium hydroxide used to neutralize a resulting reaction mixture.

SUMMARY OF THE INVENTION

An object of the present invention is to solve the abovementioned problem in the production of 1,1-bis(4-hydroxyphenyl)cyclohexanes and to provide a method for producing a 1,1-bis(4-hydroxyphenyl)cyclohexane that is highly pure and contains only a small amount of metal impurities on an industrial scale with improved production yield and efficiency.

According to the present invention, there is provided a method for producing a high purity 1,1-bis(4-hydroxyphenyl)cyclohexane represented by the general formula (II),

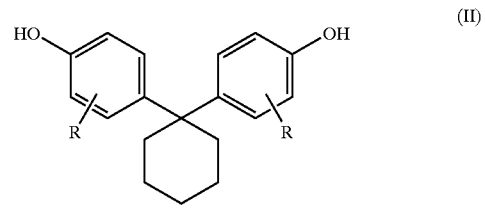

wherein R is a hydrogen atom or alkyl group,
characterized in that cyclohexanone and a phenol represented by the general formula (I),

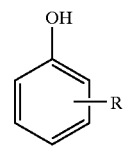

wherein R is the same as defined above,
are reacted in the presence of an acid catalyst; a reaction mixture obtained is neutralized with an alkali; a 1,1-bis(4-hydroxyphenyl)cyclohexane produced is primarily crystallized and filtered to obtain a primary crystallization filtrate; 100 parts by weight of this primary crystallization filtrate are dissolved in a mixed solvent, which comprises 5 to 10 parts by weight of water and 100 to 200 parts by weight of a lower aliphatic ketone solvent, or 200 to 400 parts by weight of a lower aliphatic alcohol solvent; the resulting solution is filtered through a zeta potential filter; and thus the 1,1-bis(4-hydroxyphenyl)cyclohexane is secondarily crystallized and filtered from the resulting filtrate in the presence of water.

DETAILED DESCRIPTION OF THE PREFERRED EMBODIMENT

A phenol to be used in the present invention is represented by the general formula (I),

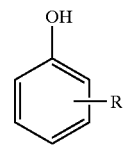

wherein R is a hydrogen atom or alkyl group.

R is a hydrogen atom or alkyl group, and when R is an alkyl group, the alkyl group has preferably 1 to 3 carbon atoms; specific examples of the alkyl group include a methyl group, ethyl group, and straight-chain or branched-chain propyl group. Accordingly, specific examples of the abovementioned phenols include phenol, 2-methylphenol, 2-ethylphenol, 2-propylphenol, and 2-isopropylphenol. Among them, phenol and 2-methylphenol are preferable and 2-methyl phenol is particularly preferable.

Upon the reaction of such a phenol with cyclohexanone, the mole ratio of the phenol to cyclohexanone is not particularly limited; however, at least higher than the theoretical value (2.0) is necessary. Generally, the ratio is in a range of 2 to 8 and more preferably in a range of 3 to 6.

According to the present invention, first, cyclohexanone and a phenol are reacted in the presence of an acid catalyst and a reaction mixture obtained is neutralized with an alkali, after which crystallization and filtration are carried out to obtain a primary crystallization filtrate.

Examples of the acid catalyst to be used in the reaction of cyclohexanone and a phenol include inorganic acids such as hydrochloric acid, hydrogen chloride, sulfuric acid, phosphoric acid, hydrogen fluoride, hydrogen bromide, boron trifluoride, and phosphorus chloride; and organic acids such as benzene sulfonate and methane sulfonate; however, concentrate hydrochloric acid, hydrogen chloride gas, 50–98% sulfuric acid, 85% phosphoric acid, methane sulfonate, and the like are preferably used. In particular, concentrate hydrochloric acid and hydrogen chloride gas are preferably used. These acid catalysts can be used singly or in combination of two or more.

In the present invention, the amount of an acid catalyst to be used is not particularly limited; however, for example, concentrate hydrochloric acid can be used in a proportion of 50 to 100% by mole to cyclohexane and hydrogen chloride gas can be used by blowing to saturation in the reaction system. Further, upon the reaction, if necessary, a cocatalyst such as aliphatic mercaptans can be used along with the abovementioned acid catalyst. Examples of the abovementioned aliphatic mercaptans include methyl mercaptan, ethyl mercaptan, propyl mercaptan, butyl mercaptan, n-octyl mercaptan, and n-dodecyl mercaptan.

According to the present invention, upon the reaction of cyclohexanone and a phenol, it is desirable to react the materials, the phenol and cyclohexanone, after sufficiently removing oxygen in the reaction system using an inert gas by a substitution method or the like, before the reaction. Generally, the reaction temperature is preferably in a range of 20 to 60° C. The reaction of a phenol and cyclohexanone can be traced using liquid chromatography analysis or gas chromatography analysis, and accordingly it is preferable to terminate the reaction at the time when unreacted cyclohexanone disappears and no more increase in the amount of the substance of interest is observed.

After cyclohexanone and a phenol are thus reacted in the presence of an acid catalyst, an alkali is added to the resulting reaction mixture to neutralize the acid catalyst. This alkali used for neutralization is not particularly limited; however, generally, a dilute alkaline aqueous solution such as a sodium hydroxide aqueous solution, potassium hydroxide aqueous solution, and sodium hydrogen phosphate aqueous solution. Among them, a sodium hydroxide aqueous solution is preferably used. The pH of the resulting reaction mixture is preferably adjusted in a range of 4 to 7 by this neutralization.

According to the present invention, after the resulting reaction mixture is neutralized in this way, the reaction product is crystallized as it is or as an adduct of the reaction product with the phenol from this reaction mixture and then filtered (primary crystallization and filtration) to obtain the reaction product as a primary crystallization filtrate from the reaction mixture.

This primary crystallization and filtration can be appropriately carried out by any method conventionally known and not particularly limited. For example, after completion of the reaction, the reaction mixture is neutralized with an alkali as mentioned above, and then the reaction product is isolated as it is or as an adduct with the phenol from the reaction mixture by filtration, washed with a mixed catalyst of the phenol and water or an aromatic hydrocarbon, and filtered to thereby obtain a primary crystallization filtrate from the reaction mixture.

Further in an alternate method, after completion of the reaction, the reaction mixture is neutralized with an alkali as mentioned above, the reaction product crystallized in the reaction mixture is dissolved as it is or as an adduct with the phenol by the addition of a catalyst, such as ketones, and heating, after which the water phase is separated from the oil phase, the solvent is removed by distillation from the residual oil phase, and then filtration is carried out to obtain a primary crystallization filtrate.

The purity of the substance of interest in the primary crystallization filtrate thus obtained is generally 95 to 98% in relation to the total amount of the substance of interest, residual phenol, byproducts and impurities. Further, metal impurities in the primary crystallization filtrate mainly consist of alkaline metals such as chlorine, iron and sodium. For example, in the case where cyclohexanone and a phenol are reacted in the presence of an acid catalyst and then a sodium hydroxide aqueous solution is added to the obtained reaction mixture for the neutralization of the acid catalyst, the content of the metal impurities in the primary crystallization filtrate is generally about 1 to 10 ppm as sodium.

According to the present invention, the primary crystallization and filtration is thus carried out to obtain a primary crystallization filtrate, and then filtration through a zeta potential filter is carried out to remove a trace amount of metal impurities from the primary crystallization filtrate obtained. A zeta potential filter to be used in the present invention can be any filter that can remove a trace amount of metal impurities by adsorption action due to the so-called zeta potential and can be used in an organic solvent. The shape of the filter is not particularly limited; for example, a filter device in which the so-called multiple cell type filter cartridges are installed in a filter housing having an inlet for the liquid to be filtered and an outlet for filtrate can be used. An example of the filter cartridge to be used as such a filter is "Zeta Plus Filter" (trade name, a product of Cuno).

Upon the filtration using a zeta potential filter, it is important that the filtration temperature is lower than 70° C. so as to be able to sufficiently remove a trace amount of metal impurities. Therefore, the crystallization temperature of the substance of interest is set to be lower than 70° C. and in order to attain industrially acceptable volumetric efficiency, 100 parts by weight of the primary crystallization filtrate obtained are dissolved in a mixed solvent, in which 5 to 10 parts by weight of water are added to 100 to 200 parts by weight of a lower aliphatic ketone that is an appropriate solvent for the substance of interest, or 200 to 400 parts by weight of a lower aliphatic alcohol solvent, so that the temperature for the crystallization of the substance of interest from such a solution is lowered to about 50 to 60° C., the volumetric efficiency within an industrially acceptable range can be attained, and thereby a trace amount of metal impurities can be removed in an industrially effective manner using the zeta potential filter.

In the present invention, the abovementioned lower aliphatic ketone is a dialkyl ketone having an alkyl group having 1 to 4 carbon atoms, and thus specific examples include acetone, methyl ethyl ketone, diethyl ketone, methyl isopropyl ketone, and methyl isobutyl ketone. Among them, in particular methyl isobutyl ketone is preferably used. Further, the abovementioned lower aliphatic alcohol solvent is an alkyl alcohol having 1 to 4 carbon atoms, and thus specific examples include methanol, ethanol, n-propanol, isopropanol, n-butanol, and 2-butanol.

In this way, the solution of the primary crystallization filtrate in the above-mentioned mixed solvent is filtered through a zeta potential filter, after which the substance of interest is crystallized from the resulting filtrate in the presence of water and then the crystals obtained are filtered (secondary crystallization and filtration); thereby a 1,1-bis (4-hydroxyphenyl)cyclohexane that is highly pure or contains an extremely small amount of metal impurities can be obtained.

In the abovementioned secondary crystallization and filtration, for example, 100 to 200 parts by weight of water are added to 100 parts by weight of the filtrate, the solvent appropriately used in the preparation of the abovementioned solvent is removed by distillation to obtain a mixture of the substance of interest and residual water, and then a solvent is further added to this mixture under normal pressure or elevated pressure for dissolution, after which cooling, crystallization and filtration are carried out. Examples of the solvent newly added to the abovementioned mixture of the substance of interest and residual water include lower aliphatic ketones and lower aliphatic alcohols used in the primary crystallization and filtration.

In this way, according to the present invention, a 1,1-bis (4-hydroxyphenyl)cyclohexane represented by the general formula (II) can be obtained corresponding to a phenol used. Thus, specific examples include 1,1-bis(4-hydroxyphenyl) cyclohexane, 1,1-bis(3-methyl-4-hydroxyphenyl) cyclohexane, 1,1-bis(3-ethyl-4-hydroxyphenyl) cyclohexane, and 1,1-bis(3-isopropyl-4-hydroxyphenyl) cyclohexane.

Particularly, according to the present invention, preferable specific examples are 1,1-bis(4-hydroxyphenyl)cyclohexane and 1,1-bis(3-methyl-4-hydroxyphenyl)cyclohexane; 1,1-bis(3-methyl-4-hydroxyphenyl)cyclohexane is particularly preferable.

In this way, according to a method of the present invention, a high purity 1,1-bis(4-hydroxyphenyl) cyclohexane that has a purity of more than 99% and contains an extremely small amount of metal impurities can be obtained; for example, as mentioned above, in the case where a sodium hydroxide aqueous solution is used to neutralize an acid catalyst in the reaction mixture obtained, a 1,1-bis(4-hydroxyphenyl)cyclohexane having an impurity metal content of less than 0.1 ppm, preferably less than 0.05 ppm, as sodium can be obtained. Further, according to the present invention, the yield in relation to the cyclohexanone material is generally more than 70%.

According to the present invention, a 1,1-bis(4-hydroxyphenyl)cyclohexane that is highly pure and contains a small amount of metal impurities can be produced advantageously on an industrial scale with improved production yield and efficiency.

EXAMPLES

The present invention will be explained by the following examples; however, these examples are not construed to limit the scope of the invention.

Reference Example 1

In a 1-L four necked flask equipped with a thermometer, dropping funnel, condenser, and stirring device were placed 194.4 g (1.8 moles) of o-cresol and 3.8 g of water, and while maintaining the inner temperature at 40° C., the air in the reaction system was replaced with nitrogen, after which hydrogen chloride gas was blown to saturation.

While maintaining the temperature at 40° C., a mixture of 58.8 g (0.6 mole) of cyclohexanone and 64.8 g (0.6 mole) of o-cresol was added dropwise over a period of 4 hours, and then the reaction was continued at the same temperature for further 18 hours.

After completion of the reaction, a 16% sodium hydroxide aqueous solution was added to the reaction mixture thus obtained for neutralization, after which 176 g of methyl isobutyl ketone were added and the temperature was raised to 100° C. to dissolve the reaction product. Next, the water layer was separated and removed from the reaction mixture and washed with water. Then water layer was removed from the mixture obtained, 92 g of water were added to the remaining oil layer, and methyl isobutyl ketone was removed by distillation, after which cooling and filtration were carried out to obtain 150 g of a primary crystallization filtrate. The purity of the substance of interest in this primary crystallization filtrate was 97% (measured by liquid chromatography), and the impurity metal sodium content was 1600 ppb (measured by atomic absorption spectrometry).

Example 1
(Purification Using Methyl Isobutyl Ketone Solvent)

In a 1-L four necked flask equipped with a thermometer, condenser, and stirring device were placed 150 g of the abovementioned primary crystallization filtrate, 225 g of methyl isobutyl ketone and 7.5 g of water, and the temperature was raised to 100° C. for dissolution. Then, while maintaining the temperature of this mixed solution at 70° C., filtration was carried out using a Cuno filter.

To the filtrate obtained were added 216 g of water, the whole amount of methyl isobutyl ketone was removed by distillation under normal pressure and then 30 g of methyl isobutyl ketone were added thereto at 90° C., after which cooling, crystallization, filtration, and drying were carried out to obtain the substance of interest, 1,1-bis(3-methyl-4-hydroxyphenyl)cyclohexane, as white crystals (melting point: 192° C. (measured by the Mettler method)). The purity was 99.9% and the metal impurity (sodium) content was 20 ppb. The yield based on the primary crystallization filtrate was 95%.

Example 2
(Purification Using Methanol Solvent)

In a 1-L four necked flask equipped with a thermometer, condenser, and stirring device were placed 150 g of the abovementioned primary crystallization filtrate and 450 g of methanol, and the temperature was raised to 65° C. for dissolution. Then, while maintaining the temperature of this mixed solution at 50° C., filtration was carried out using a Cuno filter.

From the filtrate obtained were distilled 210 g of methanol by distillation under normal pressure, and then 240 g of water were added thereto at 65° C., after which cooling, filtration, and drying were carried out to obtain the substance of interest, 1,1-bis(3-methyl-4-hydroxyphenyl)cyclohexane, as white crystals (melting point: 192° C. (measured by the Mettler method)). The purity was 99.9% and the metal impurity (sodium) content was 20 ppb. The yield based on the primary crystallization filtrate was 95%.

Comparative Example 1
(Purification Using Toluene Solvent)

In a 1-L four necked flask equipped with a thermometer, condenser, and stirring device were placed 150 g of the abovementioned primary crystallization filtrate, 300 g of toluene and 150 g of water, and the temperature was raised to 85° C. Then, while maintaining the temperature of this mixed solution at 70° C., filtration was carried out using a Cuno filter. However, the filter clogged up because crystals were not completely dissolved.

Therefore, 150 g of the abovementioned primary crystallization filtrate, 300 g of toluene and 150 g of water were placed in a 1-L four necked flask equipped with a thermometer, condenser, and stirring device, and the temperature was raised to 135° C. for dissolution. Then, this mixed solution was allowed to stand at the same temperature and the water layer was separated and removed.

Next, while stirring, a valve was gradually opened to release the pressure in the system, at the same time the remaining water in the system was recovered and crystals were separated. Then, cooling, filtration, and drying were carried out to obtain the substance of interest, 1,1-bis(3-methyl-4-hydroxyphenyl)cyclohexane, as white crystals (melting point: 192° C. (measured by the Mettler method)). The purity was 99.9% and the metal impurity (sodium) content was 200 ppb. Further, the yield base on the primary crystallization filtrate was 97%.

Comparative Example 2
(Purification Using Methanol Solvent and Without Using Cuno Filter)

In a 1-L four necked flask equipped with a thermometer, condenser, and stirring device were placed 150 g of the abovementioned primary crystallization filtrate and 450 g of methanol, and the temperature was raised to 65° C. for dissolution. Then, 210 g of methanol were removed by distillation under normal pressure, and 240 g of water were added thereto at 65° C., after which cooling, filtration, and drying were carried out to obtain the substance of interest, 1,1-bis(3-methyl-4-hydroxyphenyl)cyclohexane, as white crystals (melting point: 192° C. (measured by the Mettler method)). The purity was 99.9% and the metal impurity (sodium) content was 200 ppb. Further, the yield based on the primary crystallization filtrate was 95%.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method for producing a high purity 1,1-bis(4-hydroxyphenyl)cyclohexane represented by the general formula (II),

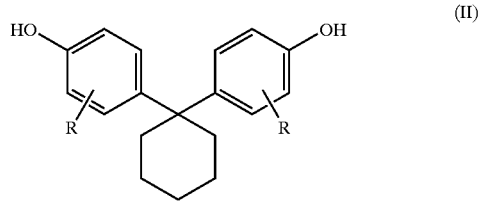

(II)

wherein R is a hydrogen atom or alkyl group, comprising the steps of:
reacting cyclohexanone and a phenol represented by the general formula (I) in the presence of an acid catalyst;

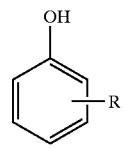

(I)

wherein R is the same as defined above,
neutralizing the resultant reaction mixture with an alkali;
primarily crystallizing and filtering a 1,1-bis(4-hydroxyphenyl)cyclohexane produced to obtain a primary crystallization filtrate;
dissolving 100 parts by weight of said primary crystallization filtrate in a mixed solvent, which comprises 5 to 10 parts by weight of water and 100 to 200 parts by weight of a lower aliphatic ketone solvent, or 200 to 400 parts by weight of a lower aliphatic alcohol solvent;
filtering the resulting solution through a zeta potential filter; and
secondarily crystallizing and filtering the 1,1-bis(4-hydroxyphenyl)cyclohexane from the resulting filtrate in the presence of water.

2. The method according to claim 1, wherein said acid catalyst is selected from the group consisting of concentrate hydrochloric acid, hydrogen chloride gas, 50–98% sulfuric acid, 85% phosphoric acid, and methane sulfonate.

3. The method according to claim 1, wherein said acid catalyst is selected from the group consisting of concentrate hydrochloric acid and hydrogen chloride gas.

4. The method according to claim 1, wherein the step of filtering by said zeta potential filter is conducted at a temperature of lower than 70° C.

5. The method according to claim 1, wherein said lower aliphatic ketone solvent is a dialkyl ketone having an alkyl group having 1 to 4 carbon atoms.

6. The method according to claim 1, wherein said lower aliphatic ketone solvent is selected from the group consisting of acetone, methyl ethyl ketone, diethyl ketone, methyl isopropyl ketone, and methyl isobutyl ketone.

7. The method according to claim 1, wherein said lower aliphatic ketone solvent is an alkyl alcohol having an alkyl group having 1 to 4 carbon atoms.

8. The method according to claim 1, wherein said lower aliphatic alcohol solvent is selected from the group consisting of methanol, ethanol, n-propanol, isopropanol, n-butanol, and 2-butanol.

* * * * *